US007179445B2

(12) United States Patent  
Collins et al.

(10) Patent No.: US 7,179,445 B2
(45) Date of Patent: *Feb. 20, 2007

(54) COBALAMIN CONJUGATES USEFUL AS IMAGING AND THERAPEUTIC AGENTS

(75) Inventors: Douglas A. Collins, Rochester, MN (US); Henricus P. C. Hogenkamp, Roseville, MN (US)

(73) Assignees: Mayo Foundation for Medical Education and Research, Rochester, MN (US); Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/785,266

(22) Filed: Feb. 24, 2004

(65) Prior Publication Data

US 2004/0166059 A1 Aug. 26, 2004

Related U.S. Application Data

(63) Continuation of application No. 09/690,353, filed on Oct. 16, 2000, now Pat. No. 6,838,073, which is a continuation-in-part of application No. PCT/US00/10098, filed on Apr. 15, 2000.

(60) Provisional application No. 60/159,753, filed on Oct. 15, 1999.

(51) Int. Cl.
*A61K 51/00* (2006.01)
*A61M 49/00* (2006.01)

(52) U.S. Cl. .................. 424/1.69; 424/1.11; 424/1.65; 424/9.1; 424/1.81; 424/1.73; 534/10; 534/14; 536/26.4

(58) Field of Classification Search ............... 424/1.11, 424/1.65, 1.73, 1.81, 1.85, 9.1; 534/7, 10–16; 514/2, 10; 536/26.4

See application file for complete search history.

(56) References Cited

U.S. PATENT DOCUMENTS

| | | | |
|---|---|---|---|
| 3,627,788 A | 12/1971 | Bouchaudon | |
| 3,936,440 A | 2/1976 | Nath | |
| 3,981,863 A | 9/1976 | Niswender et al. | |
| 4,209,614 A | 6/1980 | Bernstein et al. | |
| 4,279,859 A | 7/1981 | Gutcho et al. | |
| 4,283,342 A | 8/1981 | Yollees | |
| 4,301,140 A | 11/1981 | Frank et al. | |
| 4,465,775 A | 8/1984 | Houts | |
| 4,612,302 A | 9/1986 | Szabo et al. | |
| 4,684,620 A | 8/1987 | Hruby et al. | |
| 4,853,371 A | 8/1989 | Coy et al. | |
| 5,308,606 A | 5/1994 | Wilson et al. | |
| 5,405,598 A | 4/1995 | Schinazi et al. | |
| 5,405,839 A | 4/1995 | Toraya et al. | |
| 5,428,023 A | 6/1995 | Russell-Jones et al. | |
| 5,449,720 A | 9/1995 | Russell-Jones et al. | |
| 5,462,724 A | 10/1995 | Schinazi et al. | |
| 5,514,695 A | 5/1996 | Bergeron | |
| 5,548,064 A | 8/1996 | Russell-Jones et al. | |
| 5,574,018 A | 11/1996 | Habberfield et al. | |
| 5,589,463 A | 12/1996 | Russell-Jones et al. | |
| 5,599,796 A | 2/1997 | Schinazi et al. | |
| 5,608,060 A | 3/1997 | Axworthy et al. | |
| 5,739,313 A * | 4/1998 | Collins et al. ........... 536/26.44 |
| 5,807,832 A | 9/1998 | Russell-Jones et al. | |
| 5,840,880 A | 11/1998 | Morgan, Jr. et al. | |
| 5,869,465 A | 2/1999 | Morgan, Jr. et al. | |
| 5,869,466 A | 2/1999 | Russell-Jones et al. | |
| 5,872,107 A | 2/1999 | Schinazi et al. | |
| 5,877,165 A | 3/1999 | Miura et al. | |
| 5,936,082 A | 8/1999 | Bauer | |
| 6,004,533 A * | 12/1999 | Collins et al. ............. 424/1.73 |
| 6,074,625 A | 6/2000 | Hawthorne et al. | |
| 6,083,926 A | 7/2000 | Morgan et al. | |
| 6,083,966 A | 7/2000 | Bergeron, Jr. | |
| 6,096,290 A | 8/2000 | Collins et al. | |
| 6,150,341 A | 11/2000 | Russell-Jones et al. | |
| 6,180,766 B1 | 1/2001 | Schinazi et al. | |
| 6,211,355 B1 * | 4/2001 | Collins et al. ........... 536/26.41 |
| 6,262,253 B1 | 7/2001 | Russell-Jones et al. | |
| 6,315,978 B1 | 11/2001 | Grissom et al. | |
| 6,613,305 B1 * | 9/2003 | Collins et al. ............. 424/1.73 |
| 6,806,363 B1 * | 10/2004 | Collins et al. ............. 536/26.4 |
| 6,838,073 B1 * | 1/2005 | Collins et al. ............. 424/1.69 |
| 2002/0042394 A1 | 4/2002 | Hogenkamp et al. | |
| 2002/0049155 A1 | 4/2002 | Hogenkamp | |
| 2002/0151525 A1 | 10/2002 | Collins et al. | |
| 2003/0018009 A1 | 1/2003 | Collins | |
| 2003/0144198 A1 | 7/2003 | Collins | |

FOREIGN PATENT DOCUMENTS

AU 04490099 A1 1/2000

(Continued)

OTHER PUBLICATIONS

Alam, G. et al., "Boronated compounds for neutron capture therapy," *Strahlentherapie und Onkologie*, 165(2/3):121-123 (1989).

(Continued)

*Primary Examiner*—Dameron L. Jones
(74) *Attorney, Agent, or Firm*—Fish & Richardson P.C.

(57) ABSTRACT

The invention provides detectably labeled cobalamin derivatives which are useful for medical treatment and diagnosis.

45 Claims, 5 Drawing Sheets

FOREIGN PATENT DOCUMENTS

| | | |
|---|---|---|
| DE | 1811518 | 7/1969 |
| EP | 0 005 834 A1 | 12/1979 |
| EP | 0 069 450 A1 | 1/1983 |
| EP | 0 165 716 A1 | 12/1985 |
| JP | 58-046027 A2 | 3/1983 |
| WO | WO 89/01475 A1 | 2/1989 |
| WO | WO 92/09610 A1 | 6/1992 |
| WO | WO 92/13571 A1 | 8/1992 |
| WO | WO 94/27613 A1 | 12/1994 |
| WO | WO 94/27641 A1 | 12/1994 |
| WO | WO 96/27641 A1 | 12/1994 |
| WO | WO 95/27723 A1 | 10/1995 |
| WO | WO 96/04016 A1 | 2/1996 |
| WO | WO 96/31243 A1 | 10/1996 |
| WO | WO 97/14711 A1 | 4/1997 |
| WO | WO 97/18231 A1 | 5/1997 |
| WO | WO 97/33627 A2 | 9/1997 |
| WO | WO 98/08859 A1 | 3/1998 |
| WO | WO 99/65930 A1 | 12/1999 |
| WO | WO 00/45857 A2 | 8/2000 |
| WO | WO 00/62808 A2 | 10/2000 |
| WO | WO 00/74721 A1 | 12/2000 |
| WO | WO 01/28592 A1 | 4/2001 |
| WO | WO 01/28595 A1 | 4/2001 |
| WO | WO 01/30967 A2 | 5/2001 |
| WO | WO 01/92283 A2 | 12/2001 |
| WO | WO 01/92288 A2 | 12/2001 |
| WO | WO 02/042318 A2 | 5/2002 |
| WO | WO 02/055530 A2 | 7/2002 |
| WO | WO 03/000010 A2 | 1/2003 |
| WO | WO 03/025139 A2 | 3/2003 |

OTHER PUBLICATIONS

Allen, R.H., et al., "Isolation of gastric vitamin $B_{12}$-binding proteins using affinity chromatrography," *J. Biol. Chem.*, 248(10):3660-3669 (May 25, 1973).

Allen, R.H., et al., "Isolation of vitamin $B_{12}$-binding proteins using affinity chromatography," *J. Biol. Chem.*, 247(23):7695-7701 (Dec. 10, 1972).

Amagasaki, T., et al., "Expression of transcobalamin II receptors by human leukemia K562 and HL-60 cells," *Blood*, 76(7):1380-1386, (Oct. 1, 1990).

Anton, D.L., et al., "Carbon-13 nuclear magnetic resonance studies of the monocarboxylic acids of cyanocobalamin. Assignments of the B-, D-, and E-monocarboxylic acids," *J. Am. Chem. Soc.*, 102(7):2215-2219 (Mar. 26, 1980).

Anton, D.L., et al., "The synthesis and properties of four spin-labled analogs of adenosylcobalamin," *J. Biol. Chem.* 255(10):4507-4510 (May 25, 1980).

Begley, J.A. et al., "Cobalamin metabolism in cultured human chorionic villus cells," *J. Cell Physiol.*, 156(1):43-47 (Jul. 1993).

Bernhauer, K., et al., "Zur Chemie und Biochemie der Corrinoide," *Biochem. Z.*, 344:289-309 (1966).

Blomquist, L., et al., "Uptake of labelled vitamin B 12 and 4-iodophenylalanine in some tumors of mice," *Experientia*, 25(3):294-296 (Mar. 15, 1969).

Breeman, W.A., et al., "Indium-111 labeled DTPA- and DOTA-bombesin analogs for receptor scintigraphy and radiothereapy," in Scientific Papers (Jun. 9, 1999), Proc. of the 46th Annual Meeting of the Society of Nuclear Medicine (Los Angeles, California, Jun. 6-10, 1999), *J. Nuc. Med.*, 40(5):102P, Abstract No. 413 (May 1999 supplement).

Broan, C. J., et al., "Synthesis and complexation behaviour of an effective octadentate complexone 1,4,7,10-tetraazacyclododecane-1,4,7,10-tetrakis[methylene(methylphosphinic acid)]," *J. Chem. Soc. Chem. Comm.*, 23:1739-1741 (1990).

Collins, D.A., et al., "Transcobalamin II receptor imaging via radiolabeled diethylene-triaminepentaacetate cobalamin analogs," *J. Nucl. Med.*, 38(5):717-723 (May 1997).

Collins, D.A., et al., "Tumor imaging via indium 111-labeled DTPA-adenosylcobalamin," *Mayo Clinic Proc.*, 74(7):687-691 (Jul. 1999).

Cooper, B.A., et al., "Selective uptake of specifically bound cobalt-58 vitamin B12 by human and mouse tumour cells," *Nature*, 191, 393-395 (Jul. 1961).

De jong, M., et al., "Radionuclide therapy using radiolabeled somatostatin analogs in tumor-bearing rats," in Scientific Papers (Jun. 9, 1999), Proc. of the 46th Annual Meeting of the Society of Nuclear Medicine (Los Angeles, California, Jun. 6-10, 1999), *J. Nuc.Med.*, 40(5):102, Abstract No. 414 (May 1999 Supplement).

Ellenbogen, L., "Absorption and transport of cobalamin: Intrinsic factor and the transcobalamins," *Cobalamin: Biochemistry and Pathophysiology*, Babior, Ed., Wiley, New York (1975), Chapter 5.

Fairchild, R.G., et al., "Current status of 10-B-neutron capture therapy: enhancement of tumor dose via beam filtration and dose rate, and the effects of these parameters on minimum boron content: A theoretical evaluation," *Int. J. Radiation Oncology, Biology, Physics*, 11(4):831-840 (Apr. 1985).

Finkler, A.E., et al., "Nature of the relationship between vitamin B12 binding and cell uptake," *Arch. Biochem. Biophys.*, 120(1):79-85 (Apr. 1967).

Flodh, H., et al., "Accumulation of labelled vitamin B12 in some transplanted tumours," *Int. J. Cancer*: 3(5):694-699 (Sep. 15, 1968).

Gabel, D., "Tumor-Seeking Compounds for Boron Neutron Capture Therapy: Synthesis and Biodistribution," *Clinical Aspects of Neutron Capture Therapy*, Ralph G. Fairchild et al., eds.; Plenum Press, New York, 233-241, 1987.

Gabel, D., et al., "Monte Carlo simulation of the biological effect of the $^{10}$B(n,α)$^7$Li reaction in cells and tissue and its implication for boron neutron capture therapy," *Radiation Research*, 111:14-25 (1987).

Hall, C.A., et al., "Cyclic activity of the receptors of cobalamin bound to transcobalamin II," *J. Cell Physiol.*, 133(1):187-191 (Oct. 1987).

Hatanaka, H., "A revised boron-neutron capture therapy for malignant brain tumors," *Journal of Neurology*, 209:81-94 (1975).

Hatanaka, H., et al., "Chapter XXV: Clinical Experience of Boron-Neuron Capture Therapy for Gliomas—A Comparison with Conventional Chemo-Immuno-Radiotherapy," pp. 349-379. (undated).

Hawthorne, M.F., et al., "Preparation of tumor-specific boron compounds. 1. *In vitro* studies using boron-labeled antibodies and elemental boron as neutron target(s)," *Journal of Medicinal Chemistry*, 15(5):449-452 (1992).

Hogenkamp, H. et al., "Synthesis and Characterization of nido-Carborane-Cobalamin Conjugates," *Nucl. Med. & Biol.*, 27:89-92 (2000).

Hogenkamp, H. P. C., Chemical synthesis and properties of analogs of adenosylcobalamin, *Biochemistry*, 13(13):2736-2740 (1974).

Hogenkamp, H. P. C., et al., "Carbon-13 nuclear magentic resonance studies of adenosylcobalamin and alkylcorrinoids, selectively enriched with carbon-13," *Biochemistry*, 14(16):3707-3714 (1975).

Ichihashi, M., et al., "Specific killing effect of $^{10}B_1$-para-boronophenylalanine in thermal neutron capture therapy of malignant melanoma: In vitro radiobiological evaluation," *The Journal of Investigative Dermatology*, 78(3):215-218 (1982).

Jacobsen, D.W., et al., "Rapid purification of cobalamin-binding proteins using immobilized aminopropylcobalamin," *Anal. Biochem.*, 113:164-171 (1981).

Kikugawa, K., et al., "Direct halogenation of sugar moiety of nucleosides," *Tetrahedron Letters*, 1971)2):87-90 (1971).

Kahl, S.B., et al., "Chemical and biological studies on boronated tetraphenyl porphyrins," *Boron Chemistry*, 61-67.

Laster, B.H., et al., "Biological efficacy of a boronated porphyrin as measured in cell culture," *Strahlentherapie und Onkologie*, 165(2/3):203-205 (1989).

Lindemans, J. et al., "Uptake of transcobalamin II-bound cobalamin by HL-60 cells:effects of differentiation induction," *Experimental Cell Research*, 184(2):449-460 (Oct. 1989).

Luo, S.Z., "Studies on bone tumor therapeutic radiopharmaceuticals.IV. Investigation of the structure-activity relationships (SARS) of $^{153}$Sm-aminocarboxylate complexes," in Poster Sessions, Proc. of the 46th Annual Meeting of the Society of Nuclear Medicine (Lose Angeles, California, Jun. 6-10, 1999), *J. Nuc. Med.* 40(5):316P, Abstract No. 1386 (May 1999 supplement).

McBride, W.J., "A general method for the introduction of metal binding ligands onto the side chains of peptides during peptide synthesis," in Scientific Papers (Jun. 9, 1999), Proc. of the 46th Annual Meeting of the Society of Nuclear Medicine (Los Angeles, California, Jun. 6-10, 1999), *J. Nuc. Med.*, 40(5):124P, Abstract No. 500 (May 1999 supplement).

Mease, R.C., et al., "Indium-111 CDTA-(aminostyryl)pyridinium (di-X-asp) dyes: synthesis, canine and human leukocyte labeling, and serum stability," in Poster Sessions, Proc. of the 46th Annual Meeting of the Society of Nuclear Medicine (Los Angeles, California, Jun. 6-10, 1999), *J. Nuc.Med.*, 40(5):318P, Abstract No. 1396 (May 1999 supplement).

Mishima, Y., et al., "Treatment of malignant melanoma by single thermal neutron capture therapy with melanoma-seeking B-compound," *Lancet*, 2(8659):388-389 (Aug. 12, 1989).

Mishima, Y., et al., "First human clinical trial of melanoma neutron capture. Diagnosis and therapy," *Strahlentherapie und Onkologie*, 165(2/3):251-254 (1989).

Momen, A., et al., "Impact of high resolution bone spect imaging of the thoracolumbar spine on patient management in oncology," in Scientific Papers (Jun. 9, 1999), Proc. of the 46th Annual Meeting of the Socirty of Nuclear Medicine (Los Angeles, California, Jun, 6-10, 1999), *J. Nuc. Med.*, 40(5):124P, Abstract No. 500 (May 1999 supplement).

Nakagawa, T., et al., "Synthesis of chlorpromazine undecahydrododecaborate and nonahydrodecaborate—promising agents for neutron caoture therapy of malignant melanoma," *Chem. Pharm. Bull.(Tokyo)*, 24*4):778-781 (1976) [UDC 547.869.2.04; 547.244.04].

Nexo, E., "Cobalamin-binding proteins," Chapter 30 in *Vitamin $B_{12}$ and $B_{12}$ Proteins*, B. Krantler et al., Eds., Wiley & Sons, New York (1997), pp. 461-475.

Norenberg, J.P., "[$^{213}$Bi-DOTA$^0$, Tyr$^3$]octreotide ($^{213}$Bi-DOTATOC) in peptide receptor radionuclide therapy (PRRT)," in Scientific Papers (Jun. 9, 1999), Proc. of the 46th Annual Meeting of the society of Nuclear Medicine (Los Angeles, California, Jun. 6-10, 1999), *J. Nuc. Med.*, 40(5):103, Abstract No. 415 (May 1999 supplement).

Order, S. et al., "Use of isotopic immunoglobulin in therapy," *Cancer Res.*, 40:3001-3007 (Aug. 1980).

Pisal, S.S., et al., "Formulation of nasal gels of Vitamin B12-1: Effect of additives on thermodynamic properties of pluronic PF-127 gels," *Indian J. Pharm. Sci.* (May-Jun. 2002), accessed Nov. 12, 2002, at www.indianpharma.org/may-june2002/fnasalgels.html.

Primus, F.J., et al., "Bispecific antibody mediated targeting of *nido*-carboranes to human colon carcinoma cells," *Bioconjugate Chemistry*, 7:532-535 (1996).

Rao, P.S. et al., "TC-99M labeled peptide for imaging infection," in Poster Sessions, Proc. of the 46th Annual Meeting of the Society of Nuclear Medicine (Los Angeles, California, Jun. 6-10, 1999), *J. Nuc.Med.*, 40(5):319P, Abstract No. 1398 (May 1999 supplement).

Rappazzo, M.E., et al., "Transport function of transcobalamin II," *J. Clin. Invest.*, 51(7), 1915-1918 (Jul. 1972).

Roe, D.G., et al., "Combinatorially designed technetium radiopharmaceuticals (CDTR™)," in Scientific Papers, Proc. of the 46th Annual Meeting of the Society of Nuclear Medicine (Los Angeles, California, Jun. 6-10, 1999), *J. Nuc. Med.*, 40(5):123P, Abstract No. 499 (May 1999 supplement).

Ruser, G. et al., "Synthesis and evaluationof two new bicunctional carboxymethylatd tetrazamacrocyclic chelating agents for protein labeling with Indium-111," *Bioconj. Chem.*, 1:345-349 (1990).

Sattelberger, A.R., et al., "Nuclear medicine finds the right chemistry," *Nature Biotechnology*, 849-850, vol. 17, Sep. 1999.

Smeltzer, C.C., et al., "Synthesis and characterization of fluorescent cobalamin (CobalaFluor) derivatives for imaging," *Organic Letters*, 3(6):799-801 (2001).

Toraya, T., et al., "Preparation, properties and biological activities of succinyl derivatives of vitamin $B_{12}$,", *Bioinorg. Chem.*, 4:245-255 (1975).

Wilbur, D.S., et al., "Evaluation of Biotin-Dye Conjugates for Use in an HPLC Assay to Assess Relative Binding of Biotin Derivatives with Avidin and Streptavidin." *Bioconjugate Chem.*, 11(4), 584-598 (Jul.-Aug. 2000).

Wilbur, D.S., et al., "Biotin Reagents for Antibody Pretargeting. 4. Selection of Biotin Conjugates for in Vivo Application Based on Their Dissociation Rate from Avidin and Streptavidin." *Bioconjugate Chem.*, 11(4), 569-583 (Jul.-Aug. 2000).

Wu, C., Virzi, F., and Hnatowich, D.J., "Investigations of N-linked macrocycles for $^{111}$In and $^{90}$Y labeling of proteins," *Nucl. Med. Biol.*, 19(2):239-244 (1992) [*Int. J. Radiat. Appl. Instrum. Part B*].

Hatanaka, H., et al., "Clinical Experience of Boron Neutron Capture Therapy for Gliomas—A Comparison with Conventional Chemo-Immuno-Radiotherapy.," In: H. Hatanaka (ed.) *Boron Neutron Capture Therapy for Tumors*, Chap. 25, pp. 349-378. Niigata, Japan: Nishimura Co., Ltd. (1986).

Kahl, S.B., Micca, P., "Chemical and biological studies on boronated tetraphenyl porphyrins," in H. Hatanaka (ed.) *Boron Neutron Capture Therapy for Tumors*, pp. 61-67. Niigata, Japan: Nishimura Co., Ltd. (1986).

\* cited by examiner

Synthesis of adenosyltrifluoroethylamidocobalamins

CNCbl-COOH (b, d, and e)

| WSC
| Hydroxybenzotriazole        (1, 2, and 3)
|            +
↓ F$_3$CCH$_2$NH$_3$Cl$^-$ (4, 5, and 6)

| NaBH$_4$
| 5'-CHLORO-5'-DEOXYADENOSINE
↓

(8 and 9)

FIG. 3

Synthesis of adenosyltrifluoroethylamidocobalamins

CNCbl di COOH

| WSC
| Hydroxybenzotriazole
↓ F₃CCH₂NH₃⁺Cl⁻

Synthesis of cyano-b-trifluoroacetamidobutylamidocobalamin

| WSC
| Hydroxybenzotriazole
↓ F₃CCOO⁻Na⁺

Synthesis of cyanotrifluoroacetyl polylysine cobalamin $$\overset{+}{N}H_3-\underset{\underset{NH_3^+}{\underset{|}{(CH_2)_4}}}{\overset{\overset{H}{|}}{C}}-\overset{\overset{O}{\|}}{C}-\left[N-\underset{\underset{NH_3^+}{\underset{|}{(CH_2)_4}}}{\overset{\overset{H}{|}}{C}}-\overset{\overset{O}{\|}}{C}\right]-N-\underset{\underset{NH_3^+}{\underset{|}{(CH_2)_4}}}{\overset{\overset{H}{|}}{C}}-\overset{\overset{O}{\|}}{C}-O^-$$

↓ WSC
Hydroxybenzotriazole
CNCbl b COOH $$\overset{+}{N}H_3-\underset{\underset{\underset{CN-Cbl}{\underset{|}{C=O}}}{\underset{|}{NH}}}{\underset{\underset{|}{(CH_2)_4}}{\overset{\overset{H}{|}}{C}}}-\overset{\overset{O}{\|}}{C}-\left[N-\underset{\underset{NH_3^+}{\underset{|}{(CH_2)_4}}}{\overset{\overset{H}{|}}{C}}-\overset{\overset{O}{\|}}{C}\right]-N-\underset{\underset{NH_3^+}{\underset{|}{(CH_2)_4}}}{\overset{\overset{H}{|}}{C}}-\overset{\overset{O}{\|}}{C}-O^-$$

↓ $F_3C-\overset{\overset{O}{\|}}{C}-O-\overset{\overset{O}{\|}}{C}-CF_3$ $$\overset{+}{N}H_3-\underset{\underset{\underset{CNCbl}{\underset{|}{C=O}}}{\underset{|}{NH}}}{\underset{\underset{|}{(CH_2)_4}}{\overset{\overset{H}{|}}{C}}}-\overset{\overset{O}{\|}}{C}-\left[N-\underset{\underset{\underset{CF_3}{\underset{|}{C=O}}}{\underset{|}{NH}}}{\underset{\underset{|}{(CH_2)_4}}{\overset{\overset{H}{|}}{C}}}-\overset{\overset{O}{\|}}{C}\right]-N-\underset{\underset{\underset{CF_3}{\underset{|}{C=O}}}{\underset{|}{NH}}}{\underset{\underset{|}{(CH_2)_4}}{\overset{\overset{H}{|}}{C}}}-\overset{\overset{O}{\|}}{C}-O^-$$  (11)

FIG. 6

COBALAMIN CONJUGATES USEFUL AS IMAGING AND THERAPEUTIC AGENTS

RELATED APPLICATION

This application is a continuation of U.S. patent application Ser. No. 09/690,353, filed on Oct. 16, 2000, now U.S. Pat. No. 6,838,073 which is a continuation-in-part of PCT/US00/10098, filed on Apr. 15, 2000, and which claims priority to U.S. Provisional Application Ser. No. 60/159,753, filed 15 Oct. 1999, the disclosures of which are incorporated herein by reference.

BACKGROUND OF THE INVENTION

For several years after the isolation of vitamin $B_{12}$ as cyanocobalamin in 1948, it was assumed that cyanocobalamin and possibly hydroxocobalamin, its photolytic breakdown product, occurred in man. Since then it has been recognized that cyanocobalamin is an artifact of the isolation of vitamin $B_{12}$ and that hydroxocobalamin and the two coenzyme forms, methylcobalamin and adenosylcobalamin, are the naturally occurring forms of the vitamin.

Figure 1:
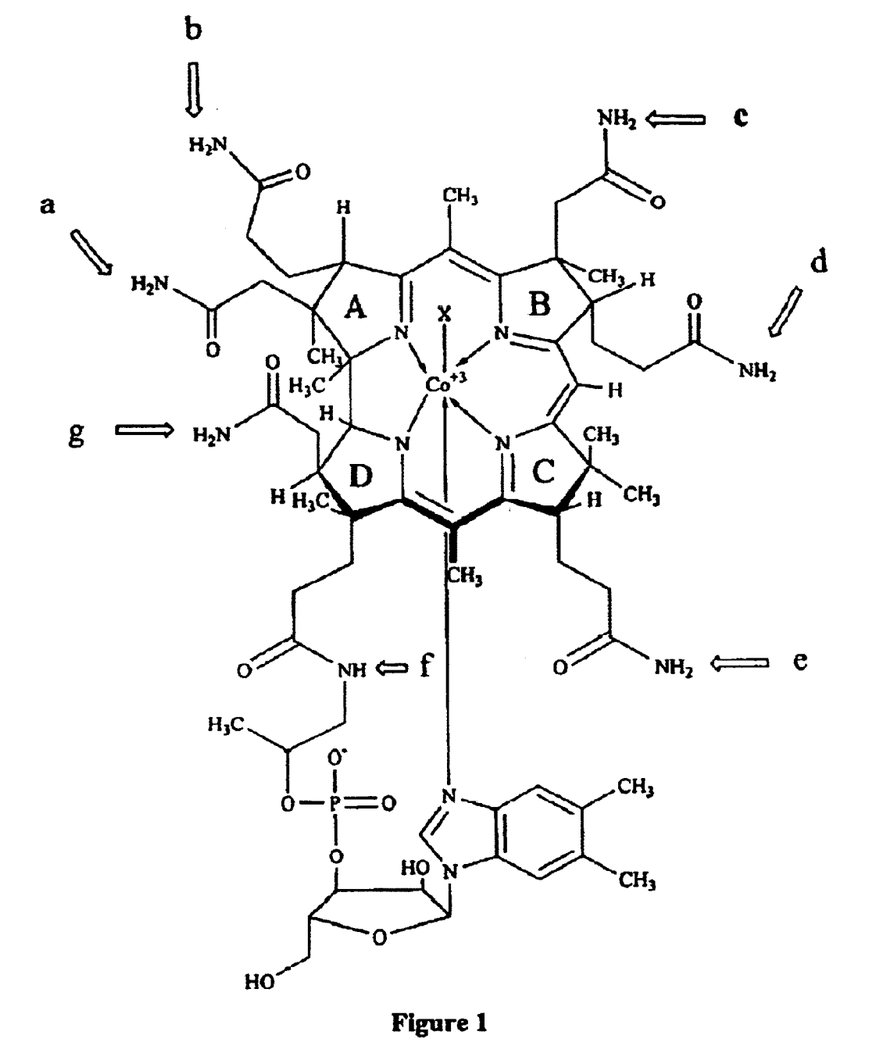
FIG. 1 illustrates a compound of formula I, wherein X is CN, OH, $CH_3$, adenosyl or a residue of a peptide or amino acid. The compound of formula I can be cyanocobalamin (X is CN), hydroxocobalamin (X is OH), methylcobalamin (X is $CH_3$), adenosylcobalamin (X is adenosyl), or a cobalamin conjugate (X is a residue of a peptide or amino acid).
Figure 2:
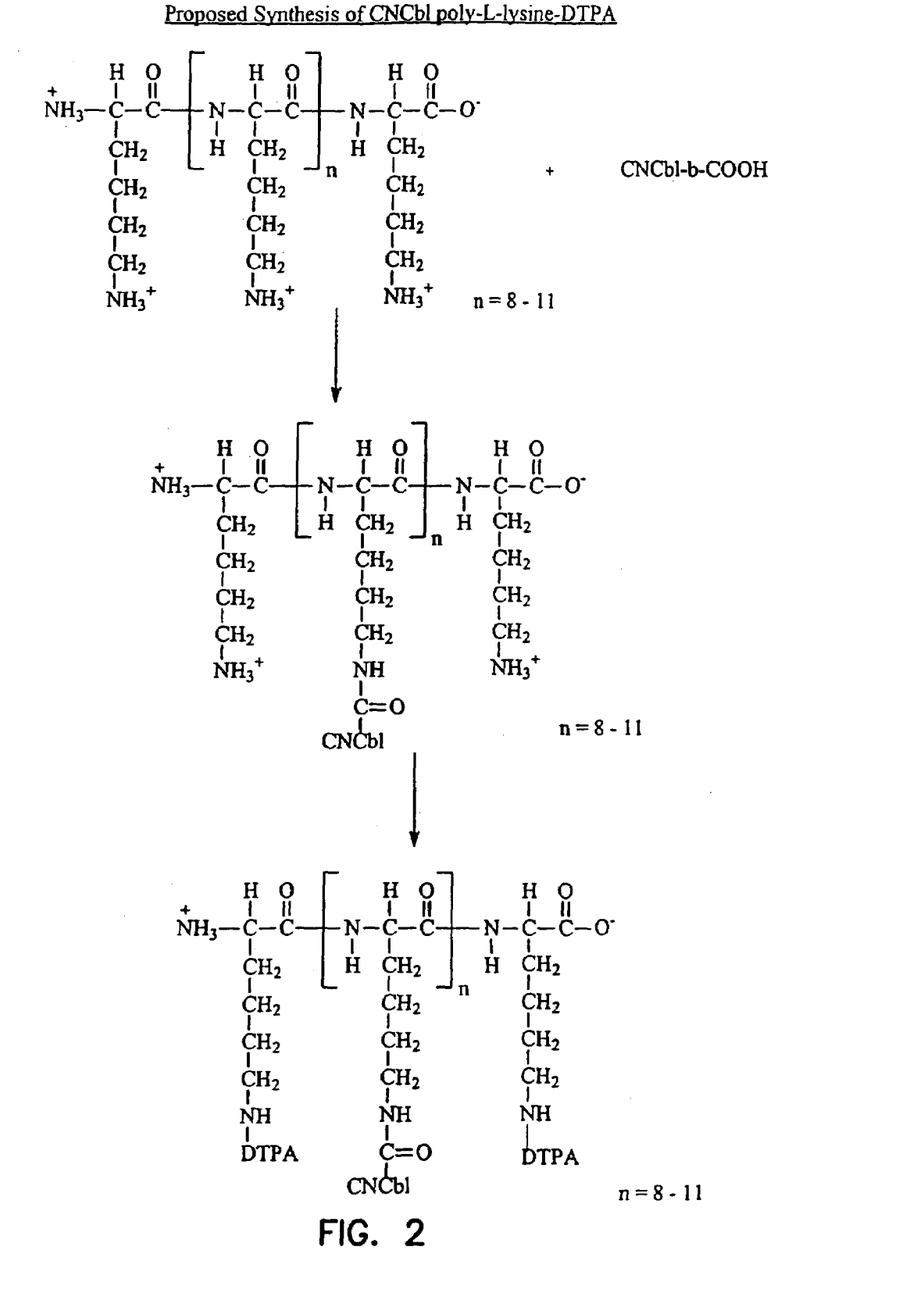
FIG. 2 illustrates a synthesis of a compound wherein a residue of a compound of formula I is linked to poly-L-lysine, 8 units to 11 units, linked to DTPA.

The structure of these various forms is shown in FIG. 1, wherein X is CN, OH, $CH_3$ or adenosyl, respectively. Hereinafter, the term cobalamin will be used to refer to all of the molecule except the X group. The fundamental ring system without cobalt (Co) or side chains is called corrin and the octadehydrocorrin is called corrole. FIG. 1 is adapted from *The Merck Index*, Merck & Co. (11th ed. 1989), wherein X is above the plane defined by the corrin ring and nucleotide is below the plane of the ring. The corrin ring has attached six amidoalkyl ($H_2NC(O)Alk$) substituents, at the 2, 3, 7, 8, 13, and 18 positions, which can be designated a–e and g, respectively. See D. L. Anton et al., *J. Amer. Chem. Soc.*, 102, 2215 (1980). The 2, 3, 7, 8, and 13 positions are shown in FIG. 1 as positions a–e, respectively.

Cells undergoing rapid proliferation have been shown to have increased uptake of thymidine and methionine. (See, for example, M. E. van Eijkeren et al., *Acta Oncologica*, 31, 539 (1992); K. Kobota et al., *J. Nucl. Med.*, 32, 2118 (1991) and K. Higashi et al., *J. Nucl. Med.*, 34, 773 (1993)). Since methylcobalamin is directly involved with methionine synthesis and indirectly involved in the synthesis of thymidylate and DNA, it is not surprising that methylcobalamin as well as Cobalt-57-cyanocobalamin have also been shown to have increased uptake in rapidly dividing tissue (for example, see, B. A. Cooper et al., *Nature*, 191, 393 (1961); H. Flodh, *Acta Radiol. Suppl.*, 284, 55 (1968); L. Bloomquist et al., *Experientia*, 25, 294 (1969)). Additionally, up-regulation in the number of transcobalamin II receptors has been demonstrated in several malignant cell lines during their accelerated thymidine incorporation and DNA synthesis (see, J. Lindemans et al., *Exp. Cell. Res.*, 184, 449 (1989); T. Amagasaki et al., *Blood*, 26, 138 (1990) and J. A. Begly et al., *J. Cell Physiol.*, 156, 43 (1993).

U.S. Pat. No. 5,739,313 discloses cobalamin analogs which comprise a compound of formula I, a linking group, a chelating group and a detectable radionuclide or a detectable paramagnetic ion. The compounds localize in tumor cells following administration and are useful for imaging tumors. Although the compounds are useful as tumor imaging agents, the specific compounds prepared therein comprise one detectable radionuclide or one detectable paramagnetic ion and thus have a limited detection capability. As such, there is a need for additional imaging agents. Particular agents will have a relatively high bioavailability, a relatively low toxicity or are detectable at a relatively low concentration. In addition, there is a need for additional therapeutic agents.

SUMMARY OF THE INVENTION

The present invention provides a series of novel cobalamin conjugates (i.e., conjugates of a residue of vitamin $B_{12}$ and a residue of a peptide or an amino acid comprising a radionuclide) that are useful to image tumors. The cobalamin conjugates have a low toxicity and a high specificity (i.e., they localize in tumor cells in higher concentration than normal cells). In addition, certain cobalamin conjugates of the invention include multiple detectable groups, so they can be detected at low concentrations.

The present invention also provides a compound wherein a residue of a compound of formula I (FIG. 1) is linked to one or more peptide residues or amino acid residues wherein: 1) at least one of the peptide residues or the amino acid residues is linked to one or more chelating groups comprising one or more metallic radionuclides; or 2) at least one of the peptide residues or the amino acid residues comprises one or more non-metallic radionuclides; or a pharmaceutically acceptable salt thereof.

The present invention also provides a compound wherein a residue of a compound of formula I (FIG. 1) is linked to one or more non-metallic radionuclides; or a pharmaceutically acceptable salt thereof;

The present invention also provides a compound (i.e., cobalamin conjugate of the present invention) wherein a residue of a compound of formula I is linked to one or more residues of the formula —[NHCH[$(CH_2)_4NH_2$-DET]-CO—]$_n$-Q wherein Q is H, ($C_1$–$C_{14}$)alkyl, or a suitable carboxy protecting group (e.g. methyl, ethyl, or benzyl; and DET is a chelating group residue comprising a metallic radionuclide and wherein n is between 2 and about 20; or a pharmaceutically acceptable salt thereof.

The present invention also provides a compound (i.e., cobalamin conjugate of the present invention) wherein a residue of a compound of formula I (FIG. 1) is linked to one or more residues of the formula wherein each M is independently a non-metallic radionuclide; each R is independently ($C_1$–$C_{14}$)alkyl, ($C_2$–$C_{14}$) alkenyl, ($C_2$–$C_{14}$)alkynyl, ($C_1$–$C_{14}$)alkoxy, hydroxy, cyano, nitro, halo, trifluoromethyl, $N(R_a)(R_b)$, ($C_1$–$C_{14}$)alkanoyl, ($C_2$–$C_{14}$)alkanoyloxy, ($C_6$–$C_{10}$)aryl, or ($C_3$–$C_8$)cycloalkyl wherein $R_a$ and $R_b$ are each independently H or ($C_1$–$C_{14}$) alkyl; Q is H, ($C_1$–$C_{14}$)alkyl, or a suitable carboxy protecting group; n is 2 to about 20; i is 1–5, j is 0–4 and i+j is ≦5; or a pharmaceutically acceptable salt thereof.

The present invention also provides a compound (i.e., cobalamin conjugate of the present invention) wherein a residue of a compound of formula I (FIG. 1) is linked to a residue of a peptide which is linked to one or more chelating groups comprising a metallic radionuclide; or a pharmaceutically acceptable salt thereof.

The present invention also provides a compound (i.e., cobalamin conjugate of the present invention) wherein a residue of a compound of formula I (FIG. 1) is linked to a residue of an amino acid which is linked to one or more chelating groups comprising a metallic radionuclide; or a pharmaceutically acceptable salt thereof.

The present invention also provides a compound (i.e., cobalamin conjugate of the present invention) wherein a residue of a compound of formula I (FIG. 1) is linked to a residue of a peptide comprising one or more non-metallic radionuclides; or a pharmaceutically acceptable salt thereof.

The present invention also provides a compound (i.e., cobalamin conjugate of the present invention) wherein a residue of a compound of formula I (FIG. 1) is linked to a residue of an amino acid comprising one or more non-metallic radionuclides; or a pharmaceutically acceptable salt thereof.

The present invention also provides a pharmaceutical composition comprising a compound of the present invention, or a pharmaceutically acceptable salt thereof; and a pharmaceutically acceptable carrier.

The present invention also provides a method of imaging a tumor in a mammal comprising administering to the mammal an effective amount of a compound of the present invention, or a pharmaceutically acceptable salt thereof; and a pharmaceutically acceptable carrier; and detecting the presence of the cobalamin conjugate.

The present invention also provides a method of treating a tumor in a mammal in need of such treatment comprising administering to the mammal an effective amount of a compound of the present invention, or a pharmaceutically acceptable salt thereof; and a pharmaceutically acceptable carrier.

The invention also provides a compound of the present invention for use in medical therapy or diagnosis.

The invention also provides the use of a compound of the present invention comprising a detectable radionuclide for the manufacture of a medicament for imaging a tumor in a mammal.

The invention also provides the use of a compound of the present invention comprising a therapeutic radionuclide for the manufacture of a medicament for treating a tumor in a mammal.

The invention also provides intermediates disclosed herein that are useful in the preparation of the compounds of the present invention as well as synthetic methods useful for preparing the compounds of the invention.

The compounds of the present invention have several characteristics which make them an attractive in vivo targeting agents. Vitamin $B_{12}$ is water soluble, has no known toxicity, and in excess is excreted by glomerular filtration. In addition, the uptake of vitamin $B_{12}$ can potentially be manipulated by the administration of nitrous oxide and other pharmacological agents (D. Swanson et al., *Pharmaceuticals in Medical Imaging*, MacMillan Pub. Co., NY (1990) at pages 621–628).

DETAILED DESCRIPTION OF THE INVENTION

The following definitions are used, unless otherwise described: halo is fluoro, chloro, bromo, or iodo. Alkyl, alkoxy, alkenyl, alkynyl, etc., denote both straight and branched groups; but reference to an individual radical such, as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

Specific and preferred values listed below for radicals, substituents, and ranges, are for illustration only; they do not exclude other defined values or other values within defined ranges for the radicals and substituents.

It is appreciated that those skilled in the art will recognize that compounds of the present invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine activity as a tumor imaging agent using the standard tests described herein, or using other similar tests which are well known in the art.

Specifically, $(C_1-C_{14})$alkyl can be methyl, ethyl, propyl, isopropyl, butyl, iso-butyl, sec-butyl, pentyl, 3-pentyl, hexyl, heptyl, octyl, nonyl, decyl undecyl, dodecyl, tridecyl or tetradecyl.

Specifically, $(C_1-C_{14})$alkoxy can be methoxy, ethoxy, propoxy, butoxy, iso-butoxy, sec-butoxy, pentoxy, 3-pentoxy, hexyloxy, heptyloxy, octyloxy, nonyloxy, decyloxy, undecyloxy, dodecyloxy, tridecyloxy, or tetradecyloxy.

Specifically, $(C_1-C_{14})$alkanoyl can be acetyl, propanoyl, butanoyl, pentanoyl, isobutanoyl, hexanoyl, heptanoyl, octanoyl, nonanoyl, decanoyl, undecanoyl, dodecanoyl, tridecanoyl, or tetradecanoyl.

Specifically, $(C_1-C_{14})$alkanoyloxy can be acetoxy, propanoyloxy, butanoyloxy, isobutanoyloxy, pentanoyloxy, hexanoyloxy, heptanoyloxy, octanoyloxy, nonanoyloxy, decanoyloxy, undecanoyloxy, dodecanoyloxy, tridecanoyloxy, or tetradecanoyloxy.

Specifically, $(C_2–C_{14})$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1- hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 1-tetradecenyl, 12-tetradecenyl or 13-tetradecenyl.

Specifically, $(C_2–C_{14})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1- hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, 1-undecynyl, 2-undecynyl, 3-undecynyl, 4-undecynyl, 5-undecynyl, 6-undecynyl, 7-undecynyl, 8-undecynyl, 9-undecynyl, 10-undecynyl, 1-dodecynyl, 2-dodecynyl, 3-dodecynyl, 4-dodecynyl, 5-dodecynyl, 6-dodecynyl, 7-dodecynyl, 8-dodecynyl, 9-dodecynyl, 10-dodecynyl, 11-dodecynyl, 1-tridecynyl, 2-tridecynyl, 3-tridecynyl, 4-tridecynyl, 5-tridecynyl, 6-tridecynyl, 7-tridecynyl, 8-tridecynyl, 9-tridecynyl, 1 0-tridecynyl, 11-tridecynyl, 12-tridecynyl, 1-tetradecynyl, 2-tetradecynyl, 3-tetradecynyl, 4-tetradecynyl, 5-tetradecynyl, 6-tetradecynyl, 7-tetradecynyl, 8-tetradecynyl, 9-tetradecynyl, 10-tetradecynyl, 11-tetradecynyl, 12-tetradecynyl or 13-tetradecynyl.

Specifically, "aryl" can be phenyl, indenyl, or naphthyl.

Specifically, $(C_3–C_8)$cycloalkyl can be cyclopropyl, cyclobutyl, cyclcopentyl, cyclohexyl, cycloheptyl or cyclooctyl.

As used herein, a "residue of a compound of formula I" is a radical of a compound of formula I having one or more open valences. Any synthetically feasible atom or atoms of the compound of formula I may be removed to provide the open valence, provided bioactivity is substantially retained. Based on the linkage that is desired, one skilled in the art can select suitably functionalized starting materials that can be derived from a compound of formula I using procedures that are known in the art. For example, suitable atoms that may be removed include the $NH_2$ group of the a-carboxamide (illustrated in FIG. 1) or a hydrogen atom from the $NH_2$ group of the a-carboxamide, the $NH_2$ group of the b-carboxamide (illustrated in FIG. 1) or a hydrogen atom from the $NH_2$ group of the b-carboxamide, the $NH_2$ group of the d-carboxamide (illustrated in FIG. 1) or a hydrogen atom from the $NH_2$ group of the d-carboxamide, the $NH_2$ group of the e-carboxamide (illustrated in FIG. 1) or a hydrogen atom from the $NH_2$ group of the e-carboxamide, and X at the 6-position (illustrated in FIG. 1). In addition, the hydrogen atom of the hydroxy group at the 3' position of the sugar, the hydrogen atom from the hydroxyl group at the 3' position of the sugar, the hydrogen atom of the $CH_2OH$ group at the 5' position, or the hydrogen atom from the hydroxyl group at the 5' position of the sugar ring may be removed.

As used herein, "adenosyl" is an adenosine radical in which any synthetically feasible atom or group of atoms have been removed, thereby providing an open valence. Synthetically feasible atoms which may be removed include the hydrogen atom of the hydroxy group at the 5' position. Accordingly, adenosyl can conveniently be attached to the 6-position of a compound of formula I via the 5' position of adenosyl.

As used herein, an "amino acid" is a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; and tert-butylglycine) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a $(C_1–C_6)$alkyl, phenyl or benzyl ester or amide). Other suitable amino and carboxy protecting groups are known to those skilled in the art (See for example, T. W. Greene, *Protecting Groups In Organic Synthesis*; Wiley: New York, 1981; D. Voet, *Biochemistry*, Wiley: New York, 1990; L. Stryer, *Biochemistry*, (3rd Ed.), W. H. Freeman and Co.: New York, 1975; J. March, *Advanced Organic Chemistry Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein). According to the invention, the amino or carboxy protecting group can also comprise a radionuclide (e.g., Fluorine-18, Iodine-123, or Iodine-124).

Specifically, when the residue of a compound of formula I is linked to a single amino acid residue linked to a chelating group comprising a metallic radionuclide, the amino acid does not have the formula $H_2N—(CH_2)_5—COOH$.

As used herein, a "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

Specifically, the peptide can be poly-L-lysine, poly-L-glutamic acid, poly-L-aspartic acid, poly-L-histidine, poly- L-ornithine, poly-L-serine, poly-L-threonine, poly-L-tyrosine, poly-L-lysine—L-phenylalanine or poly-L-lysine-L-tyrosine.

The peptide residue or amino acid residue can conveniently be linked to the residue of a compound of formula I through an amide (e.g., —N(R)C(=O)— or —C(=O)N(R)—), ester (e.g., —OC(=O)— or —C(=O)O—), ether (e.g., —O—), ketone (e.g., —C(=O)—), thioether (e.g., —S—), sulfinyl (e.g., —S(O)—), sulfonyl (e.g., —S(O)$_2$—), or a direct (e.g., C—C bond) linkage, wherein each R is independently H or (C$_1$–C$_{14}$)alkyl. Such a linkage can be formed from suitably functionalized starting materials using synthetic procedures that are known in the art. Based on the linkage that is desired, one skilled in the art can select suitably functional starting materials that can be derived from a residue of a compound of formula I and from a given peptide residue or amino acid residue using procedures that are known in the art.

The peptide residue or amino acid residue can be directly linked to any synthetically feasible position on the residue of a compound of formula I. Suitable points of attachment include, for example, the b-carboxamide, the d-carboxamide, and the e-carboxamide (illustrated in FIG. 1), as well as the 6-position (the position occupied by X in FIG. 1), and the 5'-hydroxy and the 3'-hydroxy groups on the 5-membered sugar ring, although other points of attachment are possible. U.S. Pat. No. 5,739,313 discloses compounds (e.g., cyanocobalamin-b-(4-aminobutyl)amide, methylcobalamin-b-(4-aminobutyl)amide, and adenosylcobalamin-b-(4-aminobutyl)amide) that are useful intermediates for the preparation of compounds of the present invention.

The invention also provides compounds having more than one peptide residue or amino acid residue attached to a compound of formula I. For example, the peptide residue or amino acid residue can be linked to a residue of the b-carboxamide of the compound of formula I and another peptide residue or amino acid residue can be directly linked to a residue of the d-carboxamide of the compound of formula I.

The residue of a compound of formula I can be prepared by any suitable means known in the art. For example, a monocarboxylic acid or dicarboxylic acid of cobalamin, wherein X is cyano, methyl, or adenosyl can be prepared as disclosed in U.S. Pat. No. 5,739,313. These compounds can be prepared by the mild acid hydrolysis of cyanocobalamin, which has been shown to yield a mixture of mono-, a dicarboxylic acid and one tricarboxylic acid. These carboxylic acids are derived from the propionamide side chains designated b, d and e, as discussed hereinabove, which are more susceptible to hydrolysis than the amide groups on acetamide side chains a, c, and g. The (b)-, (d)-, and (e)-monocarboxylic acids can be separated by column chromatography. See FIG. 1 hereinabove. L. Anton et al., J. Amer. Chem. Soc., 102, 2215 (1980). See, also, J. B. Armitage et al., J. Chem. Sot., 3349 (1953); K. Bernhauer, Biochem. Z., 344, 289 (1966); H. P. C. Hogenkamp et al.; Biochemistry, 14, 3707 (1975); and L. Ellenbogen, in "Cobalamin," Biochem. and Pathophysiol., B. Babior, ed., Wiley, N.Y. (1975) at chapter 5.

Compounds wherein the peptide or amino acid is linked to the 6-position of the compound of formula I can be prepared by reducing a corresponding Co (II) compound of formula I to form a nucleophilic. Co (I) compound, and treating the Co (I) compound with a suitable alkylating agent comprising an amino acid or peptide.

Particular values listed below for radicals, substituents, and ranges, are for illustration only and they do not exclude other defined values or other values within defined ranges for the radicals and substituents.

Specifically, the peptide can comprise 2 to about 20, about 5 to about 15, or about 6 to about 12 amino acids.

Specifically, the peptide can be about 5 to about 200 Angstroms, about 5 to about 150 Angstroms, about 5 to about 100 Angstroms, or about 5 to about 50 Angstroms.

Specifically, the peptide can be poly-L-lysine, comprising 2 to about 20 residues, about 5 to about 15 residues, or about 6 to about 12 residues.

Specifically, the peptide can be linked to more than one chelating group. More specifically, the peptide can be linked to 2 to about 10, 2 to about 8, 2 to about 6, or 2 to about 4 chelating groups.

Specifically, the peptide can comprise more than one non-metallic radioisotope. More specifically, the peptide can comprise 2 to about 10, 2 to about 8, 2 to about 6, or 2 to about 4 non-metallic radioisotopes.

Specifically, the amino acid can be Lys, His or Tyr.

Specifically, the amino acid can comprise more than one non-metallic radioisotope. More specifically, the amino acid can comprise 2 to about 4 non-metallic radioisotopes.

Suitable non-metallic radionuclides include Carbon-11, Fluorine-18, Bromine-76, Iodine-123, and Iodine-124.

A specific peptide residue comprising one or more non-metallic radionuclides has the following formula wherein each M is independently a suitable non-metallic radionuclide (e.g., Fluorine-18, Bromine-76, or Iodine-123); each R is independently (C$_1$–C$_{14}$)alkyl, (C$_2$–C$_{14}$)alkenyl, (C$_2$–C$_{14}$)alkynyl, (C$_1$–C$_{14}$)alkoxy, hydroxy, cyano, nitro, halo, trifluoromethyl, N(R$_a$)(R$_b$), (C$_1$–C$_{14}$)alkanoyl, (C$_2$–C$_{14}$)alkanoyloxy, (C$_6$–C$_{10}$)aryl, or (C$_3$–C$_8$)cycloalkyl wherein R$_a$ and R$_b$ are each independently H or (C$_1$–C$_{14}$) alkyl; P is H, (C$_1$–C$_{14}$)alkyl, or a suitable amino protecting group; Q is H, (C$_1$–C$_{14}$)alkyl, or a suitable carboxy protecting group; n is 2 to about 20, about 5 to about 15, or about 6 to about 12; and wherein i is 1–5, j is 0–4 and i+j is ≦5.

Specifically, i can be 1, j can be 0, M can be Fluorine-18, Bromine-76, or Iodine-123, and n can be about 6 to about 12.

Specifically, the amino acid can be linked to more than one chelating group. More specifically, the amino acid can be linked to 2 to about 10, 2 to about 8, 2 to about 6, or 2 to about 4 chelating groups.

Specifically, a conjugate of a residue of vitamin B$_{12}$ and a residue of a peptide or an amino acid comprising a radionuclide can comprise more than one chelating group. More specifically, the cobalamin conjugate can comprise 2 to about 10, 2 to about 8, 2 to about 6, or 2 to about 4 chelating groups.

Specifically, a conjugate of a residue of vitamin B$_{12}$ and a residue of a peptide or an amino acid can comprise more than one radioisotope (i.e., radionuclide). More specifically, a conjugate of a residue of vitamin B$_{12}$ and a residue of a peptide or an amino acid can comprise 2 to about 10, 2 to about 8, 2 to about 6, or 2 to about 4 radioisotopes (i.e., radionuclides).

A "detectable chelating group" is a chelating group comprising a metallic radionuclide (e.g., a metallic radioisotope) capable of detecting cancer or other neoplastic cells in vivo or in vitro. Any suitable chelating group can be employed. Specifically, the chelating group can be NTA, HEDTA, DCTA, RP414, MDP, DOTATOC, CDTA, HYNIC, EDTA, DTPA, TETA, DOTA, DCTA, 15N4, 9N3, 12N3, or MAG3 (or another suitable polyamino acid chelator), which are described herein below, or a phosphonate chelator (e.g. EDMT). More specifically, the chelating group can be DTPA.

DTPA is diethylenetriaminetetraacetic acid; TETA is 1,4,8,11-tetraazacyclotetradecane-N,N',N'',N'''-tetraacetic acid; DOTA is 1,4,7,10-tetraazacyclododecane-N,N',N'',N'''-tetraacetic acid; 15N4 is 1,4,8,12-tetraazacyclopentadecane-N,N',N'',N'''-tetraacetic acid; 9N3 is 1,4,7-triazacyclononane-N,N',N''-triacetic acid; 12N3 is 1,5,9-triazacyclododecane-N,N',N''-triacetic acid; MAG3 is (N—[N—[N-[(benzoylthio) acetyl]glycyl]glycyl]glycine);and DCTA is a cyclohexane-based metal chelator of the formula wherein $R^3$ may by $(C_1-C_4)$alkyl or $CH_2CO_2$—, which may be attached through positions 4 or 5, or through the group $R^3$ and which carries from 1 to 4 detectable metal or nonmetal cations (M), monovalent cations, or the alkaline earth metals. Thus, with metals of oxidation state +1, each individual cyclohexane-based molecule may carry up to 4 metal cations (where both $R^3$ groups are $CH_2COOM$). As is more likely, with higher oxidation states, the number of metals will decrease to 2 or even 1 per cyclohexane skeleton. This formula is not intended to limit the molecule to any specific stereochemistry. NTA, HEDTA, and DCTA are disclosed in Poster Sessions, Proceedings of the 46th Annual Meeting, *J. Nuc. Med.*, p. 316, No. 1386. RP414 is disclosed in Scientific Papers, Proceedings of the 46th Annual Meeting, *J. Nuc. Med.*, p. 123, No. 499. MDP is disclosed in Scientific Papers, Proceedings of the 46th Annual Meeting, *J. Nuc. Med.*, p. 102, No. 413. DOTATOC is disclosed in Scientific Papers, Proceedings of the 46th Annual Meeting, *J. Nuc. Med.*, p. 102, No. 414 and Scientific Papers, Proceedings of the 46th Annual Meeting, *J. Nuc. Med.*, p. 103, No. 415. CDTA is disclosed in Poster Sessions, Proceedings of the 46th Annual Meeting, *J. Nuc. Med.*, p. 318, No. 1396. HYNIC is disclosed in Poster Sessions, Proceedings of the 46th Annual Meeting, *J. Nuc. Med.*, p. 319, No. 1398.

Bifunctional chelators based on macrocyclic ligands in which conjugation is via an activated arm attached to the carbon backbone of the ligand can also be employed as a chelating group, as described by M. Moi et al., *J. Amer. Chem. Soc.*, 49, 2639 (1989) (2-p-nitrobenzyl-1,4,7,10-tetraazacyclododecane-N,N',N'',N'''-tetraacetic acid); S. V. Deshpande et al., *J. Nucl. Med.*, 31, 473 (1990); G. Kuser et al., Bioconj. Chem., 1, 345 (1990); C. J. Broan et al., *J. C. S. Chem. Comm.*, 23, 1739 (1990); and C. J. Anderson et al., *J. Nucl. Med.*, 36, 850 (1995) (6-bromoacetamido-benzyl-1,4,8,11-tetraaza-cyclotetadecane-N,N',N'',N'''-tetraacetic acid (BAT)).

In addition, the diagnostic chelator or therapeutic chelator can be any of the chelators disclosed in Scientific Papers, Proceedings of the 46th Annual Meeting, *J. Nuc. Med.*, Wednesday, Jun. 9, 1999, p. 124, No. 500.

Suitable metallic radionuclides (i.e., metallic radioisotopes or metallic paramagnetic ions) include Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-i99, Hafnium-175, Hafnium-175–181, Holmium-166, Iridium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

Specifically, the chelating group can comprise more than one metallic radioisotope. More specifically, the chelating group can comprise 2 to about 10, 2 to about 8, 2 to about 6, or 2 to about 4 metallic radioisotopes.

As used herein, a "detectable chelating group" is a chelating group comprising a metallic radionuclide (e.g., a metallic radioisotope) capable of detecting cancer or other neoplastic cells in a diagnostic procedure in vivo or in vitro. Any suitable chelating group can be employed. Specifically, the chelating group can be NTA, HEDTA, DCTA, RP414, MDP, DOTATOC, CDTA, HYNIC, EDTA, DTPA, TETA, DOTA, DOTM, DCTA, 15N4, 9N3, 12N3, or MAG3. More specifically, the chelating group can be DTPA.

As used herein, a "detectable radionuclide" is any suitable radionuclide (i.e., radioisotope) capable of detecting cancer or other neoplastic cells in a diagnostic procedure in vivo or in vitro. Suitable detectable radionuclides include metallic radionuclides (i.e., metallic radioisotopes) and non-metallic radionuclides (i.e., non-metallic radioisotopes).

Specifically, the non-metallic radionuclide can be a non-metallic paramagnetic atom (e.g., Fluorine-19); or a non-metallic positron emitting radionuclide (e.g., Carbon-11, Fluorine-18, Iodine-123, or Bromine-76). Fluorine-18 is a suitable non-metallic radionuclide for use the compounds of the present invention in part because there is typically little or no background noise associated with the diagnostic use of fluorine in the body of a mammal (e.g., human).

Specifically, the metallic radionuclide can be a diagnostic gamma emitter (e.g., Tc-99m, In-111, Iodine-131, or Iron-59); a diagnostic metallic positron emitting radionuclide (e.g., Bismuth-206, Bismuth-207, Cobalt-55, Gallium-64, Copper-67, Yttrium-86, or Yttrium-88); or a paramagnetic diagnosis metal ion (e.g., Europium-152 or Gadolinium-157).

As used herein, a "therapeutic radionuclide" is any suitable radionuclide (i.e., radioisotope) that possesses therapeutic efficacy against cancer or other neoplastic cells in vivo or in vitro. Suitable therapeutic radionuclides include metallic radionuclides (i.e., metallic radioisotopes).

Specifically, the metallic radionuclide can be a therapeutic metallic radionuclide (e.g., Actinium-223, Bismuth-212, Indium-111, Rhenium-186, Rhenium-188, Strontium-89, Tin-117m, and Yttrium-90) or a therapeutic paramagnetic metal ion (e.g., Gadolinium-157).

Specifically, the chelating group can be any one of the carbonyl complexes disclosed in Waibel et al., *Nature Biotechnology*, 897–901, Vol. 17, September 1999; or Sattelberger et al., *Nature Biotechnology*, 849–850, Vol. 17, September 1999.

Specifically, the chelating group can be any of the carbonyl complexes disclosed in Waibel et al., *Nature Biotechnology*, 897–901; Vol. 17, September 1999; or Sattelberger et al., *Nature Biotechnology*, 849–850, Vol. 17, September 1999, further comprising a metallic radionuclide. More specifically, the chelating group can be any of the carbonyl complexes disclosed in Waibel et al., *Nature Biotechnology*, 897–901, Vol. 17, September 1999; or Sattelberger et al., *Nature Biotechnology*, 849–850, Vol. 17, September 1999, further comprising Technetium-99m.

Specifically, the chelating group can be any of the carbonyl complexes disclosed in Waibel et al., *Nature Biotechnology*, 897–901, Vol. 17, September 1999; or Sattelberger et al., *Nature Biotechnology*, 849–850, Vol. 17, September 1999, further comprising a metallic radionuclide. More specifically, the chelating group can be any of the carbonyl complexes disclosed in Waibel et al., *Nature Biotechnology*, 897–901, Vol. 17, September 1999; or Sattelberger et al., *Nature Biotechnology*, 849–850, Vol. 17, September 1999.

Specifically, the chelating group can be DTPA and n can be 8 to 11.

The invention provides compounds wherein a residue of a compound of formula I is linked to a radionuclide. For such a compound, the radionuclide (e.g., detectable radionuclide) can be linked, directly or through a linker, to the residue of a compound of formula I.

A directly linked detectable radionuclide can be linked directly to any synthetically feasible position on the residue of a compound of formula I. Suitable points of attachment include, for example, the b-carboxamide, the d-carboxamide, and the e-carboxamide (illustrated in FIG. 1), as well as the 6-position (the position occupied by X in FIG. 1), and the 5'-hydroxy and the 3'-hydroxy groups on the 5-membered sugar ring, although other points of attachment are possible. U.S. Pat. No. 5,739,313 discloses compounds (e.g., cyanocobalamin-b-(4-aminobutyl)amide, methylcobalamin-b-(4-aminobutyl)amide, and adenosylcobalamin-b-(4-aminobutyl)amide) that are useful intermediates for the preparation of compounds of the present invention.

When a radionuclide is linked to the residue of a compound of formula I by a suitable linker, the structure of the linker is not crucial, provided it provides a compound of the invention which has an effective therapeutic and/or diagnostic index against the target cells, and which will localize in or near tumor molecules.

Suitable linkers include linkers that separate the residue of a compound of formula I and the detectable radionuclide by about 5 angstroms to about 200 angstroms, inclusive, in length. Other suitable linkers include linkers that separate the residue of a compound of formula I and the detectable radionuclide by about 5 angstroms to about 100 angstroms, as well as linkers that separate the residue of a compound of formula I and the detectable radionuclide by about 5 angstroms to about 50 angstroms, or by about 5 angstroms to about 25 angstroms. Suitable linkers are disclosed, for example, in U.S. Pat. No. 5,735,313.

Specifically, the linker can be a divalent radical of the formula W-A wherein A is $(C_1-C_6)$alkyl, $(C_2-C_6)$alkenyl, $(C_2-C_6)$alkynyl, $(C_3-C_8)$cycloalkyl, or $(C_6-C_{10})$aryl, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or $(C_1-C_6)$alkyl; wherein A is linked to one or more non-metallic radionuclides.

The compounds disclosed herein can be prepared using procedures similar to those described in U.S. Pat. No. 5,739,313, or using procedures similar to those described herein. Additional intermediates and synthetic preparations useful for preparing compounds of the present invention are disclosed, for example, in Hogenkamp, H. et al., *Synthesis and Characterization of nido-Carborane-Cobalamin Conjugates*, Nucl. Med. & Biol., 2000, 27, 89–92; Collins, D., et al., *Tumor Imaging Via Indium 111-Labeled DTPA-Adenosylcobalamin*, Mayo Clinic Proc., 1999, 74:687–691; U.S. Application Ser. No. 60/129,733 filed 16 Apr. 1999; U.S. Application Ser. No. 60/159,874 filed 15 Oct. 1999; U.S. Application Ser. No. 60/159,753 filed 15 Oct. 1999; U.S. Application Ser. No. 60/159,873 filed 15 Oct. 1999; and references cited therein.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The present invention provides a method of imaging a tumor in a mammal. The tumor can be located in any part of the mammal. Specifically, the tumor can be located in the breast, lung, thyroid, lymph node, genitourinary system (e.g., kidney, ureter, bladder, ovary, teste, or prostate), musculoskeletal system (e.g., bones, skeletal muscle, or bone marrow), gastrointestinal tract. (e.g., stomach, esophagus, small bowel, colon, rectum, pancreas, liver, or smooth muscle), central or peripheral nervous system (e.g., brain, spinal cord, or nerves), head and neck tumors (e.g., ears, eyes, nasopharynx, oropharynx, or salivary glands), or the heart.

The compound of the present invention (cobalamin conjugates) can be formulated as pharmaceutical compositions and administered to a mammalian host, such as a human patient in a variety of forms adapted to the chosen route of administration, i.e., by intravenous, intramuscular, or subcutaneous routes.

The cobalamin conjugates can be administered intravenously or intraperitoneally by infusion or injection. Solutions of the substance can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions comprising the substance which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, normal saline, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the substance in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Depending on the diagnostic radionuclide utilized to label the cobalamin peptide conjugates, the suitable dose ranges between 500 µCi to 20 mCi. This is based on both human and swine biodistribution studies (D A Collins, H P C Hogenkamp, M W Gebard, Tumor Imaging Indium-111-labeled DTPA-adenosylcobalamin, Mayo Clinic Proceedings, 1999; 74; 687–691; Biodistribution of Radiolabeled Adenosylcobalamin in Humans, Review of 30 patents submitted to Mayo Clinic Proceedings).

The invention will now be illustrated by the following non-limiting Examples.

EXAMPLES

Poly-L-lysine hydrobromide (MW 500–2000) and (MW 1000–4000), adenosine, 1-ethyl-3(3'-dimethylaminopropyl) carbodiimide, trifluoroacetic acid, trifluoroacetic anhydride, 2,2,2-trifluoroethylamine hydrochloride and 1-hydroxybenzotriazole were purchased from Sigma. Chemical Co. Sephodex-G-10 was purchased from Pharmacia Biotech, Inc. Thin layer chromatography (TLC) silica gel plates were obtained from Eastman Kodak Co. Solvents and other reagents were obtained in the highest purity available. Cyanocobalamin-b, d and e monocarboxylic acid and the b,d-dicarboxylic acid were prepared as described before (Anton, D. L., Hogenkamp, H. P. C., Walker, T. E. and Matwiyoff, N. A., Carbon-13 nuclear magnetic resonance studies of the monocarboxylic acids of cyanocobalamin. Assignments of the b-, d-, and e-monocarboxylic acids, *J. Am. Chem. Soc.*, 102, 2215–2219 (1980)). 5' chloro-5'-deoxyadenosine was synthesized by the method of Kikugawa and Ichino (Kikugawa, K. and Ichino, M., *Tetrahedron Lett.*, 87 (1971)). The adenosylcobalamin-monocarboxylic acid was prepared as described before (Hogenkamp, H. P. C., Chemical synthesis and properties of analogs of adenosylcobalamin, *Biochemistry*, 13, 2736–2740 (1974)).

Example 1

Cyanocobalamin-Poly L-Lysine-DTPA Conjugate. Poly-L-lysine hydrobromide (Sigma no. PO879), degree of polymerization ~11 units, molecular weight range 1000–4000 (500 mg) was dissolved in water (20 ml). Cyanocobalamin-b-monocarboxylic acid (150 mg, ~100 µmol), 1-ethyl-3 (3'-dimethylaminopropyl) carbodiimide (480 mg, 2.5 mmol) and hydroxybenzo-triazole (338 mg, 2.5 mmol) were added. The pH of the mixture was adjusted and maintained at approximately 8 with 1 N sodium hydroxide. The progress of the reaction was monitored by thin layer chromatography on silica gel sheets using isopropanol-ammonium hydroxide-water (7:1:2) as the developing agent.

Upon completion of the reaction, the mixture was applied to a column of Sephadex G-10 (3×40 cm). The column was eluted with water and 2 ml fractions were collected. The red eluents that reacted with ninhydrin were pooled and freeze dried (i.e., lyophilized).

Recovery of the cyanocobalamin-poly-L-lysine complex (about 70%) was obtained. The cyanocobalamin-poly-L-lysine complex was dissolved in water (10 ml) and a saturated solution of sodium bicarbonate (10 ml) and DTPA bisanhydride (Sigma) (375 mg, 1 mmol) were added.

The progress of the reaction was monitored by TLC as described above. The cyanocobalamin-poly-L-lysine-DTPA conjugate was purified on Sephadex G-10 as described above. The final product was freeze dried and isolated as a red powder.

Example 2

Cyanocobalamin-Poly L-Lysine-DTPA Conjugate. Poly-L-lysine (Sigma no. 8954) degree of polymerization ~8 units, molecular weight range 500–2000 (500 mg) was dissolved in water (20 ml). Cyanocobalamin-b-mondcarboxylic acid (150 mg, ~100 µmols), 1-ethyl-3 (3'-dimethylaminopropyl) carbodiimide (480 mg, 2.5 mmol) and hydroxybenzotriazole (338 mg, 2.5 mmol) were added. The pH of the mixture was adjusted and maintained at approximately 8 with 1 N sodium hydroxide. The progress of the reaction was monitored by thin layer chromatography on silica gel sheets using isopropanol-ammonium hydroxide-water (7:1:2) as the developing agent.

Upon completion of the reaction, the mixture was applied to a column of Sephadex G-10 (3×40 cm). The column was eluted with water and 2 ml fractions were collected. The red eluents that reacted with ninhydrin were pooled and freeze dried (i.e., lyophilized).

Recovery of the cyanocobalamin-poly-L-lysine complex (about 70%) was obtained. The cyanocobalamin-poly-L-lysine complex was dissolved in water (10 ml) and a saturated solution of sodium bicarbonate (10 ml) and DTPA bisanhydride (Sigma) (375 mg, mmol) were added.

The progress of the reaction was monitored by TLC as described above. The cyanocobalamin-poly-L-lysine-DTPA conjugate was purified on Sephadex G-10 as described above. The final product was freeze dried and isolated as a red powder.

Example 3

Imaging Data. In vitro unsaturated B12 binding capacity (UBBC) has demonstrated that cyanocobalamin-poly-L-lysine, cyanocobalamin-poly-L-lysine-polyDTPA compounds have in vitro biological activity that is 92% and 43.4% when compared to cyanocobalamin. Comparison of cyanocobalamin-DTPA to cyanocobalamin was 66.4% (Transcobalamin II receptor imaging via radiolabeled diethylene-triaminepentaacetate cobalamin analogs, *J. Nucl. Med.*, 38, 717–723 (1997); also described in U.S. Pat. No.5,739,313). The specific activity has been increased from 300 µCi in the cobalamin mono-DTPA compounds to 4.5 mCi with the cobalamin poly-L-lysine-polyDTPA complex (D A Collins, HPC Hogenkamp, M W Gebard, Tumor Imaging Indium-111-labeled DTPA-adenosylcobalamin, Mayo Clinic Proceedings, 1999; 74; 687–691; Biodistribution of Radiolabeled Adenosylcobalamin in Humans, Review of 30 patents submitted to Mayo Clinic Proceedings). This should improve tumor-to-background ratio, which can be evaluated in murine tumor models. Attachment of either the adenosyl and methyl group as the beta ligand should improve the biological activity as it did with the cyanocobalamin mono-DTPA compound (Transcobalamin II receptor imaging via radiolabeled diethylene-triaminepentaacetate cobalamin analogs, *J. Nucl. Med.*, 38, 717–723 (1997); also described in U.S. Pat. No. 5,739,313).

Example 4

Synthesis of Adenosyltrifluoroethylamidocobalamins

Figure 3:
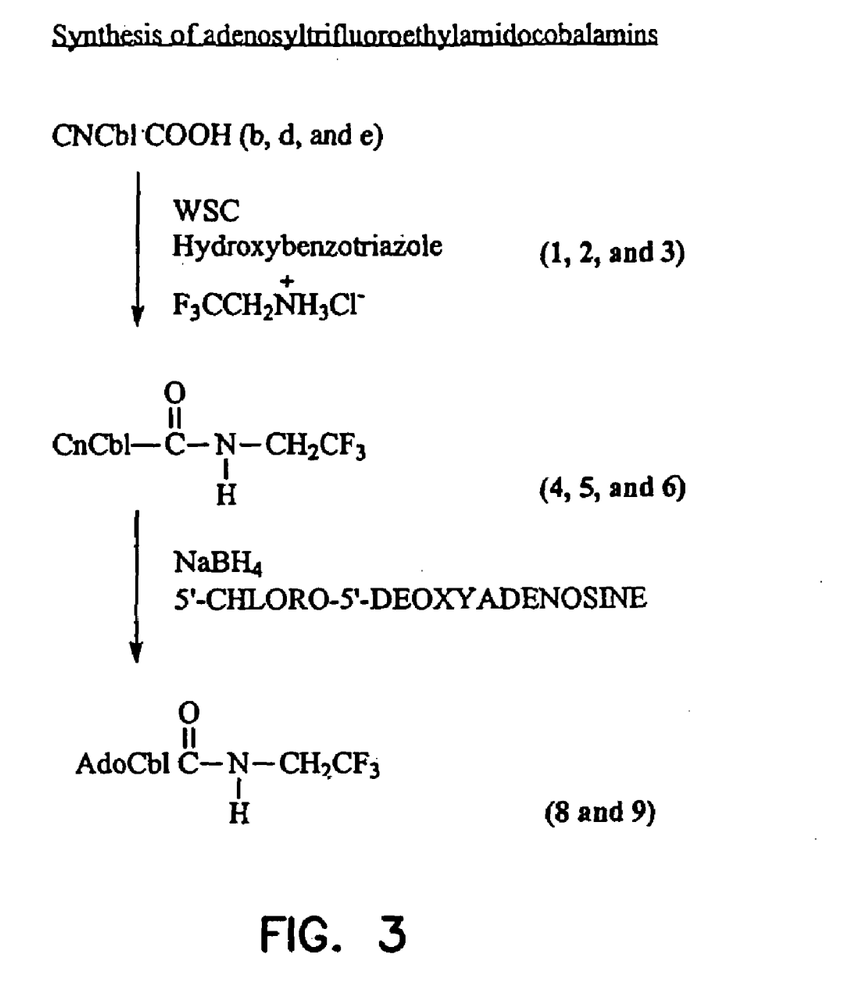
FIG. 3 illustrates a synthesis of representative compounds of the invention (8, 9) wherein a residue of a compound of formula I is linked to a non-metallic radionuclide (e.g., Fluorine-18).

Adenosyltrifluoroethylamidocobalamins (compounds 8 and 9, FIG. 3). Separately the b- and e-cyanotrifluoroethylamidocobalamins (compounds 5,6) 500 mg (~0.33 mmol) were reduced with sodium borohydride to their cobalt (I) forms, which in turn were reacted with 5' chloro-5'-deoxyadenosine as described before (Hogeikamp, H. P. C., Chemical synthesis and properties of analogs of adenosylcobalamin, *Biochemistry*, 13, 2736–2740 (1974)). The reaction mixtures were acidified to pH 3 with 1N HCl and applied to separate columns of A6 50×2 (200–400 mesh, pH 3.0). The columns were washed with water and the desired adenosylcobalamins eluted with 0.1 M sodium acetate pH 6A. After desalting by extraction into phenol as described above, both 8 and 9 were isolated as red powders. Yields 315 mg and 320 mg respectively.

The intermediates, compounds 4, 5, and 6, were prepared as follows:

(A.) Cyanotrifluoroethylamidocobalamin (compounds 4, 5, and 6, FIG. 3). Separate reaction mixtures containing 600 mg (~0.4 mmol) of the b, d and e-cyanocobalamin mono-carboxylic acids (compounds 1, 2, 3, FIG. 3), hydroxybenzotriazole 540 mg (4 mmol), 1-ethyl-3(3'-dimethylaminopropyl) carbodiimide 768 mg (4 mmol) and 2,2,2-trifluoroethylamino hydrochloride 678 mg (5 mmol) were dissolved in 50 mL water and the pH adjusted to 6.8 with 1N NaOH. The progress of the reactions was monitored by TLC using 2-propanol-$NH_4OH$-water (7:1:2) as the solvent. After 2 hr incubation at room temperature, the mixtures were extracted into 92% aqueous phenol. The phenol layers were extensively washed with water to remove the water-soluble reagents. One volume of acetone and three volumes of ether were then added to the phenol phases and the desired fluorocobalamins were back extracted into water. The aqueous phases were extracted three times with ether to remove residual phenol. The solutions were concentrated on a rotary evaporator and the fluorocobalamins crystallized from aqueous acetone. Yields 4, 600 mg; 5, 540 mg; 6, 470 mg.

Example 5

Figure 5:
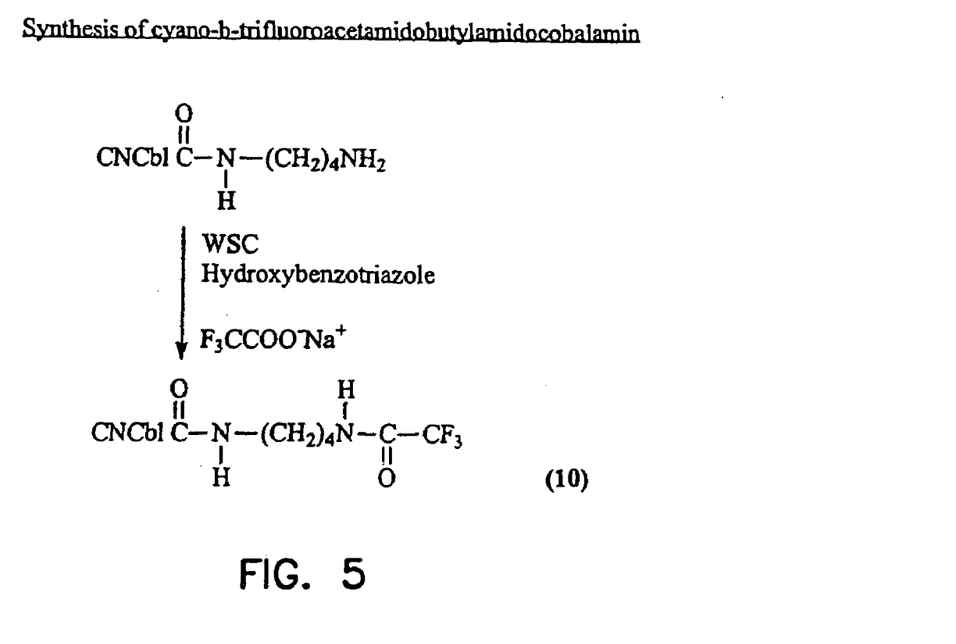
FIG. 5 illustrates a synthesis of a compound of the present invention (10) wherein a residue of a compound of formula I is linked to a non-metallic radionuclide (e.g., Fluorine-18) through a linker.

Cyano-b-trifluoroacetamide butylamide cobalamin (compound 10, FIG. 5). Cyanocobalamin-b-(9-aminobutyl) amide (600 mg, ~0.4 mmol) was prepared as described by Collins, D. A. and Hogenkamp, H. P. C., Transcobalamin II receptor imaging via radiolabeled diethylenetriaminepentaacetate cobalamin analogs, *J. Nucl. Med.*, 38, 717–723 (1997), hydroxybenzotriazole 540 mg (4 mmol), 1-ethyl-3 (3'-dimethylaminopropyl) carbodiimide 768 mg (4 mmol) and sodium trifluoroacetate (680 mg, 5 mmol) were dissolved in 50 mL water and the pH adjusted to 6.2 with 1N NaOH. After incubation at room temperature for 5 hr, the reaction mixture was desalted as described above. The resulting aqueous solution was purified by column chromatography (A6, 50×2, 200–400 mesh, pH 3.0) and the pass through collected. The solution was concentrated and compound 10 was crystallized from aqueous acetone. Yield 315 mg.

Example 6

Figure 4:
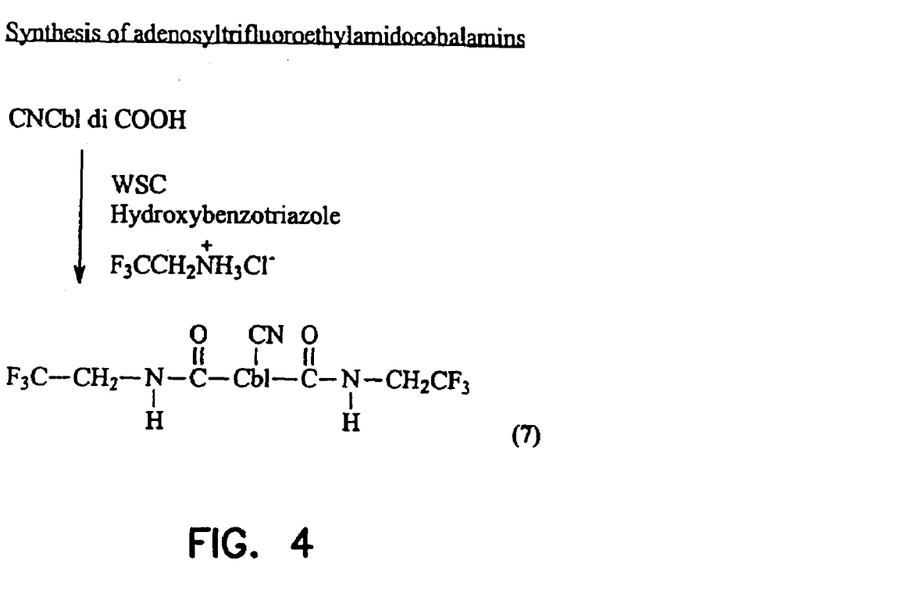
FIG. 4 illustrates a synthesis of a compound of the present invention (7) wherein a residue of a compound of formula I is linked to a non-metallic radionuclide (e.g., Fluorine-18) through a linker.

Cyano-bis-trifluoroethylamidocobalamin (compound 7, FIG. 4). A reaction mixture containing cyanocobalamin-b, d-dicarboxylic acid (540 mg, ~0.36 mmol) was reacted with 2,2,2-trifluoroethylamine hydrochloride 678 mg (5 mmol) as described above, compound 7 was crystallized from aqueous acetone. Yield 630 mg.

Example 7

Figure 6:
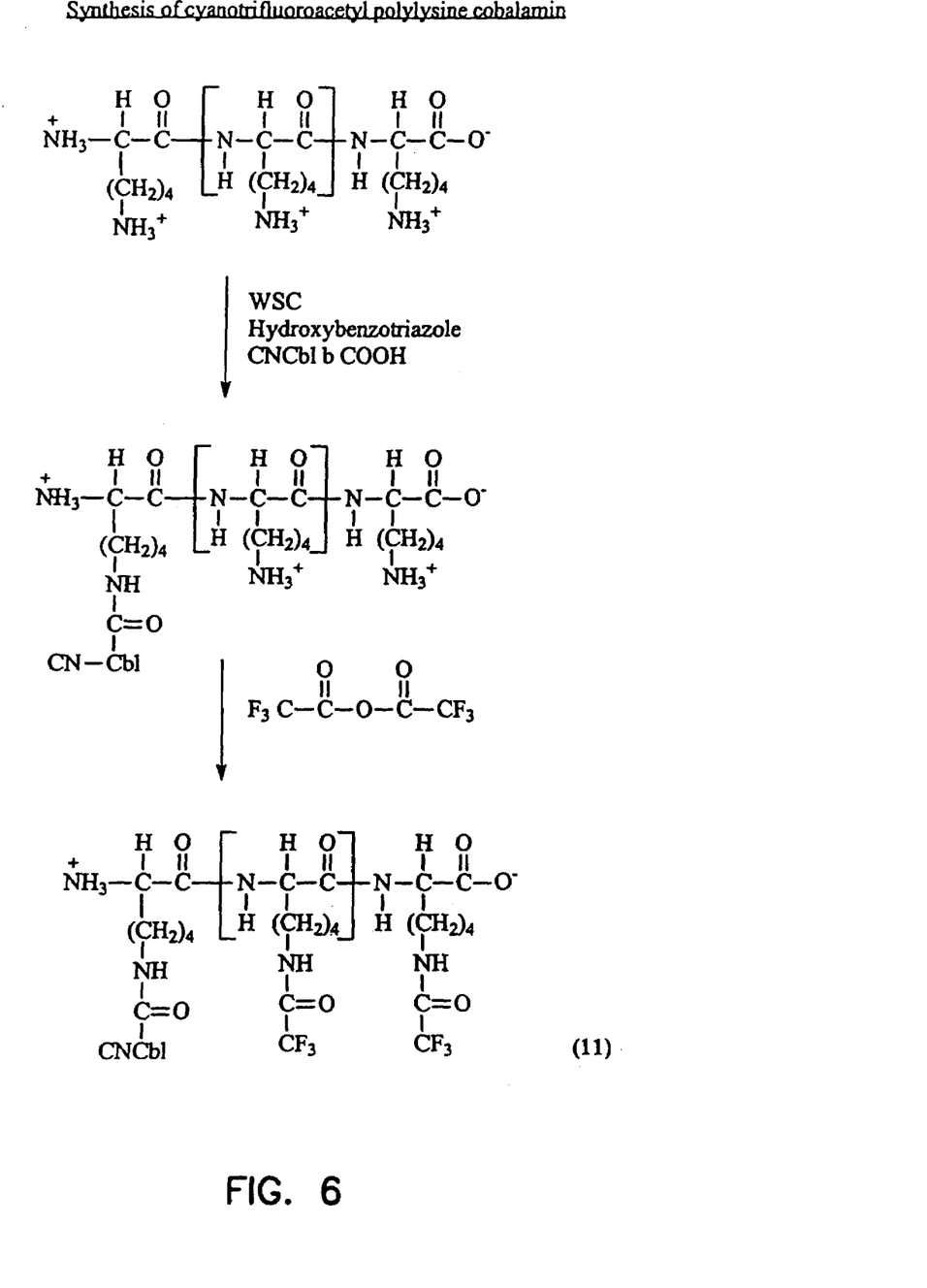
FIG. 6 illustrates a synthesis of a compound of the present invention (11) wherein a residue of a compound of formula I is linked to a peptide residue that comprises a non-metallic radionuclide (e.g., Fluorine-18).

Cyanotrifluoroacetyl polylysine cobalamin (compound 11, FIG. 6). Poly-L-lysine hydrobromide (MW 500–2000) 500 mg, cyanocobalamin-b-carboxylic acid 300 mg (~0.2 mmol), hydroxybenzotriazole (338 mg, 2.5 mmol) and 1-ethyl-3(3'-dimethylaminopropyl) carbodiimide 480 mg (2.5 mmol) were dissolved in 10 mL of water and the pH adjusted to 6.5 with 1N NaOH. After incubation at room temperature for 4 hr, the reaction mixture was purified by chromatography (Sephodex G-10, 40×3 cm), which was eluted with water. The red eluents, that also reacted with ninhydrin, were pooled and freeze dried. The freeze-dried preparation was dissolved in 10 mL saturated sodium bicarbonate and reacted with 1 mL of trifluoroacetic anhydride for 1 hr. The preparation was again purified by chromatography and lyophilized to yield 490 mg of compound 11 as a fluffy powder.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound wherein a residue of a compound of formula I:

formula 1 is linked to one or more peptide residues or amino acid residues wherein: at least one of the peptide residues or the amino acid residues comprises one or more non-metallic radionuclides; and wherein X is CN, OH, $CH_3$ or adenosyl; or a pharmaceutically acceptable salt thereof; and
   wherein a–g identify carboxamide positions in the compound.

2. The compound of claim 1 wherein at least one of the one or more non-metallic radionuclides is a diagnostic radionuclide.

3. The compound of claim 1 wherein the residue of a compound of formula I is linked to a peptide residue or an amino acid residue at the position of the b-carboxamide, d-carboxamide, e-carboxamide, or the 6-position of the compound of formula I.

4. The compound of claim 1 wherein the residue of a compound of formula I is linked to a peptide residue or an amino acid residue at the position of the b-carboxamide of the compound of formula I.

5. The compound of claim 1 wherein the residue of a compound of formula I is linked to a peptide residue or an amino acid residue at the d-carboxamide of the compound of formula I.

6. The compound of claim 1 wherein the residue of a compound of formula I is linked to a peptide residue or an amino acid residue at the e-carboxamide of the compound of formula I.

7. The compound of claim 1 wherein the residue of a compound of formula I is linked to a peptide residue or an amino acid residue at the 6-position of the compound of formula I.

8. The compound of claim 1 wherein at least one peptide residue comprises 2 to about 20 amino acids.

9. The compound of claim 8 wherein at least one peptide residue is a residue of poly-L-lysine.

10. The compound of claim 1 wherein at least one peptide residue comprises more than one non-metallic radionuclide.

11. The compound of claim 1 wherein at least one amino acid residue comprises more than one non-metallic radionuclide.

12. The compound of claim 1 wherein at least one peptide residue comprises 2 to about 4 non-metallic radionuclides.

13. The compound of claim 1 wherein at least one amino acid residue comprises 2 to about 4 non-metallic radionuclides.

14. The compound of claim 1 wherein each non-metallic radionuclide is independently Fluorine-18, Bromine-76, or Iodine-123.

15. The compound of claim 1 wherein the residue of a compound of formula I is linked to two peptide residues, two amino acid residues, or a peptide residue and an amino acid residue wherein at least one of the peptide residues or at least one of the amino acid residues comprises one or more non-metallic radionuclides.

16. The compound of claim 1 wherein at least one peptide residue has the formula wherein each M is independently a non-metallic radionuclide; each R is independently $(C_1-C_{14})$alkyl, $(C_2-C_{14})$alkenyl, $(C_2-C_{14})$alkynyl, $(C_1-C_{14})$alkoxy, hydroxy, cyano, nitro, halo, trifluoromethyl, $N(R_a)(R_b)$, $(C_1-C_{14})$alkanoyl, $(C_2-C_{14})$alkanoyloxy, $(C_6-C_{10})$aryl, or $(C_3-C_8)$cycloalkyl wherein $R_a$ and $R_b$ are each independently H or $(C_1-C_{14})$alkyl; Q is H, $(C_1-C_{14})$alkyl, or suitable amino protecting group; n is 2 to about 20; and wherein i is 1–5, j is 0–4 and i+j is $\leq 5$.

17. The compound of claim 16 wherein each M is independently Fluorine-18, Bromine-76, or Iodine-123.

18. A compound wherein a residue of a compound of formula I:

formula 1 wherein X is CN, OH, CH₃ or adenosyl; or a pharmaceutically acceptable salt thereof; is linked to one or more residues of the formula

—[NHCH[CH₂]CO]ₙ—Q wherein each M is independently a non-metallic radionuclide; wherein each R is independently (C₁–C₁₄)alkyl, (C₂–C₄)alkenyl, (C₂–C₁₄)alkynyl, (C₁–C₁₄)alkoxy, hydroxy, cyano, nitro, halo, trifluoromethyl, N(Rₐ)(R_b), (C₁–C₁₄)alkanoyl, (C₂–C₁₄)alkanoyloxy, (C₆–C₁₀)aryl, or (C₃–C₈)cycloalkyl wherein Rₐ and R_b are each independently H or (C₁–C₁₄)alkyl; Q is H, (C₁–C₁₄)alkyl, or a suitable amino protecting group; n is 2 to about 20; and wherein i is 1–5, j is 0–4 and i+j is ≦5; or a pharmaceutically acceptable salt thereof.

19. The compound of claim 18 wherein each M is Fluorine-18, Bromine-76, or Iodine-123.

20. The compound of claim 18 wherein i is 1.

21. The compound of claim 18 wherein j is 0.

22. The compound of claim 1 wherein the residue of a compound of formula I is further linked to one or more detectable radionuclides.

23. The compound of claim 22 wherein the detectable radionuclide is a non-metallic radionuclide.

24. The compound of claim 23 wherein the non-metallic radionuclide is Carbon-11, Fluorine-18, Bromine-76, Iodine-123, or Iodine-124.

25. The compound of claim 22 wherein the detectable radionuclide is directly linked to the compound of formula I.

26. The compound of claim 22 wherein the detectable radionuclide is linked by a linker to the compound of formula I.

27. The compound of claim 26 wherein the linker is of the formula W-A wherein A is (C₁–C₆)alkyl, (C₂–C₆)alkenyl, (C₂–C₆)alkynyl, (C₃–C₈)cyclo-alkyl, or (C₆–C₁₀)aryl, wherein W is —N(R)C(=O)—, —C(=O)N(R)—, —OC(=O)—, —C(=O)O—, —O—, —S—, —S(O)—, —S(O)₂—, —N(R)—, —C(=O)—, or a direct bond; wherein each R is independently H or (C₁–C₆)alkyl; and wherein A is linked to one or more non-metallic radionuclides.

28. The compound of claim 26 wherein the linker is about 5 angstroms to about 50 angstroms, inclusive, in length.

29. The compound of claim 26 wherein the linker is linked to the 6-position of the compound of formula I or is linked to the residue of a-, b-, d- or e-carboxamide group of the compound of formula I.

30. A compound of claim 1, wherein a residue of a compound of formula I is linked to a residue of a peptide comprising one or more non-metallic radionuclides; or a pharmaceutically acceptable salt thereof.

31. A compound of claim 1, wherein a residue of a compound of formula I is linked to a residue of an amino acid comprising one or more non-metallic radionuclides; or a pharmaceutically acceptable salt thereof.

32. A compound of claim 1, wherein a residue of a compound of formula I is linked to one or more non-metallic radionuclides; or a pharmaceutically acceptable salt thereof.

33. The compound of claim 32 wherein the non-metallic radionuclide is Carbon-11, Fluorine-18, Bromine-76, Iodine-123, or Iodine-124.

34. The compound of claim 32 wherein the detectable radionuclide is directly linked to the compound of formula I.

35. The compound of claim 32 wherein the detectable radionuclide is linked by a linker to the compound of formula I.

36. The compound of claim 35 wherein the linker is of the formula W-A wherein A is (C₁–C₆)alkyl, (C₂–C₆)alkenyl, (C₂–C₆)alkynyl, (C₃–C₈)cyclo-alkyl, or (C₆–C₁₀)aryl, wherein W is —N(R)C(=O)—, —C(=O)N(R)—, —OC(=O)—, —C(=O)O—, —O—, —S—, —S(O)—, —S(O)₂—, —N(R)—, —C(=O)—, or a direct bond; wherein each R is independently H or (C₁–C₆)alkyl; and wherein A is linked to one or more non-metallic radionuclides.

37. The compound of claim 35 wherein the linker is about 5 angstroms to about 50 angstroms, inclusive, in length.

38. The compound of claim 35 wherein the linker is linked to the 6-position of the compound of formula I or is linked to the residue of a-, b-, d- or e-carboxamide group of the compound of formula I.

39. A pharmaceutical composition comprising a compound of claim 1 and a pharmaceutically acceptable carrier.

40. A method for imaging a tumor in mammalian tissue comprising administering to the mammal an amount of a compound of claim 1; and detecting said compound.

41. The method of claim 40 wherein the mammal is a human.

42. The method of claim 40 wherein the mammalian tissue is located in the breast, lung, thyroid, lymph node, genitourinary system, musculoskeletal system, gastrointestinal tract, central or peripheral nervous system, head, neck, or heart.

43. A method for treating a tumor in a mammal comprising administering to the mammal an effective therapeutic amount of a compound of claim 1; wherein said compound comprises at lease one therapeutic radionuclide.

44. The method of claim 43 wherein the mammal is a human.

45. The method of claim 43 wherein the mammalian tissue is located in the breast, lung, thyroid, lymph node, genitourinary system, musculoskeletal system, gastrointestinal tract, central or peripheral nervous system, head, neck, or heart.

* * * * *

UNITED STATES PATENT AND TRADEMARK OFFICE
CERTIFICATE OF CORRECTION

PATENT NO. : 7,179,445 B2
APPLICATION NO. : 10/785266
DATED : February 20, 2007
INVENTOR(S) : Douglas A. Collins and Henricus P.C. Hogenkamp It is certified that error appears in the above-identified patent and that said Letters Patent is hereby corrected as shown below:

Title Page (Page 2), References Cited, Foreign Patent Documents, WO 96/27641, please delete "12/1994" and insert --12/1996-- therefor;

Title Page (Page 2), References Cited, Other Publications, first Allen et al. reference, please delete "chromatrography" and insert --chromatography-- therefor;

Title Page (Page 2), References Cited, Other Publications, Breeman et al. reference, please delete "radiothereapy" and insert --radiotherapy-- therefor;

Title Page (Page 3), References Cited, Other Publications, Mease et al. reference, please delete "pyridiniumum" and insert --pyridinium-- therefor;

Title Page (Page 3), References Cited, Other Publications, Nakagawa et al. reference, please delete "caoture" and insert --capture-- therefor;

Title Page (Page 3), References Cited, Other Publications, Nakagawa et al. reference, please delete "24*4)" and insert --24(4)-- therefor;

Title Page (Page 3), References Cited, Other Publications, Ruser et al. reference, please delete "bicunctional carboxymethylatd" and insert --bifunctional carboxymethylated-- therefor;

Column 18, line 42, after "or" please insert --a--;

Column 18, line 44, please delete "<" and insert --≦-- therefor;

Column 19, line 37, please delete "<" and insert --≦-- therefor;

UNITED STATES PATENT AND TRADEMARK OFFICE
CERTIFICATE OF CORRECTION

PATENT NO. : 7,179,445 B2
APPLICATION NO. : 10/785266
DATED : February 20, 2007
INVENTOR(S) : Douglas A. Collins and Henricus P.C. Hogenkamp It is certified that error appears in the above-identified patent and that said Letters Patent is hereby corrected as shown below:

Column 20, line 57, please delete "lease" and insert --least-- therefor.

Signed and Sealed this

Twenty-first Day of August, 2007

JON W. DUDAS
*Director of the United States Patent and Trademark Office*